(12) United States Patent
Ward et al.

(10) Patent No.: US 6,268,498 B1
(45) Date of Patent: Jul. 31, 2001

(54) PROCESS FOR THE PREPARATION OF GRANISETRON

(75) Inventors: Neal Ward, Crowborough; David Alan Jones, Sevenoaks; Victor Witold Jacewicz, Tunbridge Wells, all of (GB)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/125,199
(22) PCT Filed: Feb. 11, 1997
(86) PCT No.: PCT/GB97/00380
  § 371 Date: Mar. 23, 2000
  § 102(e) Date: Mar. 23, 2000
(87) PCT Pub. No.: WO97/30049
  PCT Pub. Date: Aug. 21, 1997

(30) Foreign Application Priority Data

Feb. 13, 1996 (GB) .................................................. 9602866

(51) Int. Cl.⁷ ........................ C07D 221/02; C07D 401/04
(52) U.S. Cl. ............................ 546/112; 546/112; 546/126
(58) Field of Search .............................................. 546/112

(56) References Cited

FOREIGN PATENT DOCUMENTS 0 200 444 A2  4/1986  (EP) .

*Primary Examiner*—Alan L. Rotman
(74) *Attorney, Agent, or Firm*—George W. Johnston; Patricia S. Rocha-Tramaloni; Robert A. Silverman

(57) ABSTRACT

A process for preparing granisetron by cyclising a compound of structure (2).

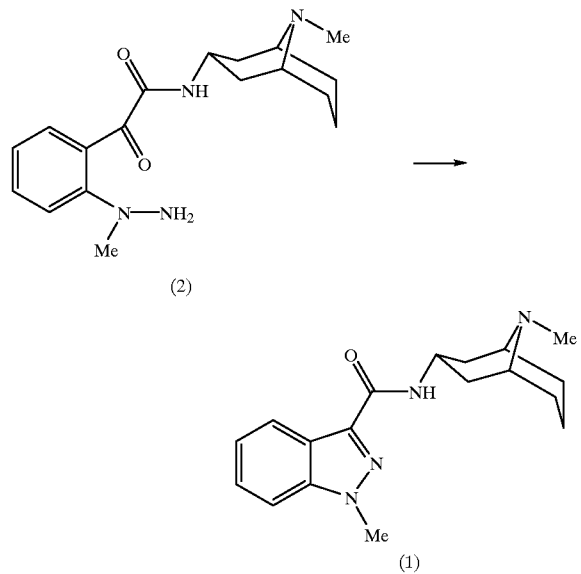

5 Claims, No Drawings

PROCESS FOR THE PREPARATION OF GRANISETRON

The present invention relates to a new process for preparing pharmaceutically active compounds and intermediates therefor.

EP-A-0200 444 (Beecham Group plc) describes certain 5-HT (5-hydroxytryptamine) antagonists which are described as possessing a number of therapeutic utilities, inter alia the prevention of vomiting following the administration of cytotoxic agents. The compound described in Example 6 is endo-N-(9-methyl-9-azabicyclo[3.3.1]non-3-yl)-1-methylindazole-3-carboxamide, and this compound has been assigned the INN granisetron. EP-A-0200 444 discloses that granisetron can be prepared by reacting 1-methylindazole-3-carboxylic acid chloride with endo-3-amino-9-methyl-9-azabicyclo[3.3.1]nonane.

A new process has been devised which can be used to prepare granisetron in a high state of purity. Accordingly, the present invention provides a process for preparing granisetron (1) or a pharmaceutically acceptable salt thereof:

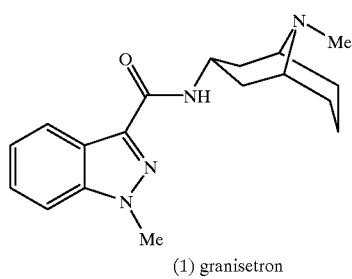

(1) granisetron which process comprises cyclising a compound of structure (2).

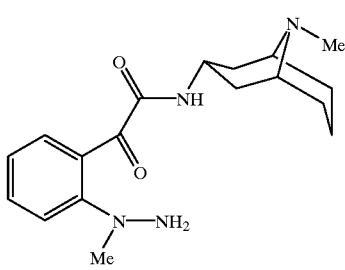

(2)

The cyclisation proceeds spontaneously under the conditions of deprotection.

The compound of structure (2) is conveniently prepared from a compound of structure (3)

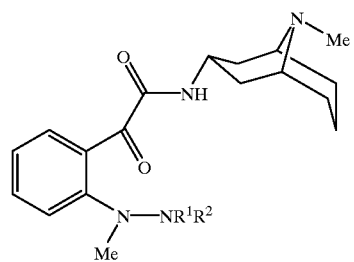

(3)

in which $R^1$ and $R^2$ together form the group $=CHR$ in which R is $C_{1-4}$ alkyl such as methyl or ethyl or aryl such as optionally substituted phenyl, or $R^1$ and $R^2$ together form an oxygen atom:

(a) the compound is prepared in situ by deprotecting a hydrazone, suitably by carrying out deprotection under aqueous acidic conditions; or (b) by the reduction of a nitroso compound of structure (3) in which $R^1$ and $R^2$ together are an oxygen atom, for example with either a solution of tin (II) chloride in dilute hydrochloric acid or a solution of sodium dithionite.

The intermediate compound of structure (2) and compounds of structure (3) in which $R^1$ and $R^2$ together form the group $=CHR$ and in which $R^1$ and $R^2$ together are an oxygen atom are novel and form a part of this invention.

The hydrazones of structure (3) in which $R^1$ and $R^2$ together form the group $=CHR$ can be prepared according to the procedure described in Annalen (1978) (2) pages 280–282 by reacting a compound of structure (4) with endo-3-amino-9-methyl-9-azabicyclo[3.3.1]nonane (5) and methylating the resulting product.

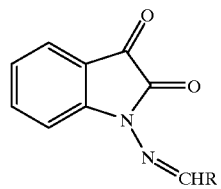

(4)

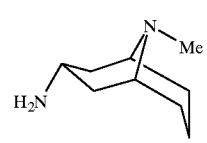

(5)

The compound of Structure (3) in which $R^1$ and $R^2$ together form an oxygen atom may be prepared by reacting a compound of structure (6) with a solution of sodium nitrite and acidifying the mixture.

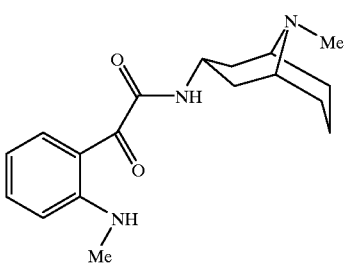

(6)

Compound (6) may be prepared by, for example, Friedel-Crafts reaction of a dichloroborane derivative of N-methylaniline with methyl oxalyl chloride, followed by reaction with endo-3-amino-9-methyl-9-azabicyclo[3.3.1]nonane (5) in DMSO; an alternative process is by direct Friedel-Crafts reaction of a dichloroborane derivative of N-methylaniline with a suitably activated derivative of the oxalamide of structure (7).

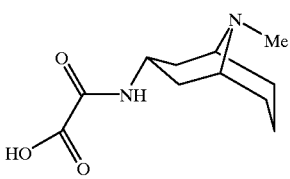

(7)

In this specification compounds are shown in the boat-chair form. It will be recognised that these conformations will be in equilibrium with the corresponding chair-chair forms which are shown in EP-A-0200444.

The invention is illustrated and in no way limited by the following Examples:

EXAMPLE 1

Preparation of 2-(N-methylbenzylidenehydrazo)-α-oxophenyl-(9-methyl-9-azabicyclo[3.3.1]non-3-yl) carboxamide (compound (3), $R^1$ and $R^2$ together representing =CHPh).

(a) A solution of 1-(phenylmethyleneamino)isatin (1.354 g, 0.0054 mol) and endo-3-amino-9-methyl-9-azabicyclo[3.3.1]nonane (0.832 g, 0.0054 mol) in dry tetrahydrofuran (25 ml) under argon was heated to reflux for 5 hours. The solution was cooled and evaporated and the residual traces of tetrahydrofuran were azeotropically removed with dichloromethane (2×10 ml). The residue was triturated with ether to give the intermediate 2-(benzylidenehydrazino)-α-oxophenyl-(9-methyl-9-azabicyclo[3.3.1]non-3-yl) carboxamide as an orange powder (1.583 g, 73%). MS 405 (M+H)$^+$, IR (nujol mull, cm$^{-1}$) 3249 (NH), 1667, 1656, 1567, 1513, 1377.

(b) Sodium hydride (50 mg, 60% dispersion in oil) was added to a solution of the 2-(benzylidenehydrazino)-a-oxophenyl-(9-methyl-9-azabicyclo[3.3.1]non-3-yl) carboxamide in dry tetrahydrofuran (2.3 ml) under argon at −50° C. The resultant solution was warmed to 0° C. over 20 minutes then cooled to −30° C. and treated with methyl iodide (0.020 ml). The solution was allowed to warm to room temperature and stirred for 24 hours then filtered. The filtrate was evaporated to dryness, and triturated with chloroform to give the title compound as a light coloured powder (50 mg, 38%). Further trituration of the mother liquor gave a further crop, (37 mg, 28%, after recrystallisation from chloroform). MS 419 (M+H)$^+$, IR (nujol mull, cm$^{-1}$) 3249 (NH)1656, 1620, 1565, 1516, 1376.

EXAMPLE 2

Preparation of endo-N-(9-methyl-9-azabicyclo[3.3.1]non-3-yl)-1-methylindazole-3-carboxamide (granisetron).

A solution of 2-(N-methylbenzylidenehydrazo)-α-oxophenyl-(9-methyl-9-azabicyclo[3.3.1]non-3-yl) carboxamide (37 mg) in methanol (1 ml) was treated with 2N hydrochloric acid (0.1 ml) and left at room temperature for several hours. Evaporation of the solvent gave the crude product as a brown oil (36 mg). HPLC and MS analysis confirmed the structure and indicated a quantitative yield of endo-N-(9-methyl-9-azabicyclo[3.3.1]non-3-yl)-1-methylindazole-3-carboxamide.

EXAMPLE 3

Preparation of endo-N-(9-methyl-9-azabicyclo[3.3.1]non-3-yl)-indazole-3-carboxamide.

A solution of 2-(N-methylbenzylidenehydrazino)-α-oxophenyl-[endo-N-(9-methyl-9-azabicyclo[3.3.1]non-3-yl)] carboxamide(0.536 g) in methanol (8 ml) was treated with 2N hydrochloric acid (0.4 ml) at room temperature. A rapid colour change from orange to green was observed. The solution was stirred for 24 hours then evaporated to the give the crude endo-N-(9-methyl-9-azabicyclo[3.3.1]non-3-yl)-indazole-3-carboxamide (0.630 g).

EXAMPLE 4

Preparation of endo-N-(9-methyl-9-azabicyclo[3.3.1]non-3-yl)-1-methylindazole-3-carboxamide (granisetron).

Sodium hydride (72 mg, 60% dispersion in oil) was added to a solution of endo-N-(9-methyl-9-azabicyclo[3.3.1]non-3-yl)-indazole-3-carboxamide (0.130 g) in dry tetrahydrofuran (3.0 ml) under nitrogen at −50° C. The resultant solution was warmed to room temperature over 20 minutes then cooled to −40° C. and treated with methyl iodide (0.015 ml). After 3 hours at room temperature HPLC analysis showed complete conversion to endo-N-(9-methyl-9-azabicyclo[3.3.1]non-3-yl)-1-methylindazole-3-carboxamide. Water (10 ml) was added and the mixture extracted with ethyl acetate (2×20 ml). The extracts were dried (MgSO$_4$) and evaporated to give endo-N-(9-methyl-9-azabicyclo[3.3.1]non-3-yl)-1-methylindazole-3-carboxamide 50 mg (41%). MS 313 (M+H)$^+$.

What is claimed is:

1. A process for preparing granisetron (1) or a pharmaceutically acceptable salt thereof:

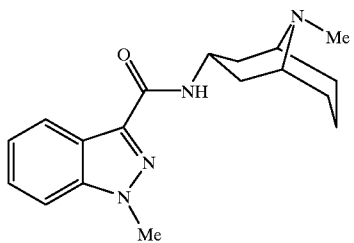

(1) granisetron which process comprises cyclising under conditions of deprotection a compound of structure (2):

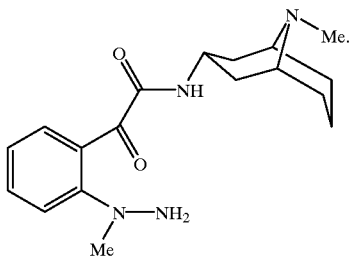
(2)

2. A process according to claim 1 in which the compound of structure (2) is prepared in situ by deprotecting under aqueous acidic conditions a protected derivative of structure (3):

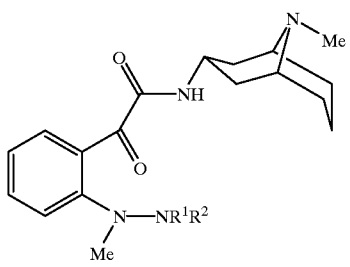
(3)

in which $R^1$ and $R^2$ together form the group =CHR in which R is $C_{1-4}$ alkyl or aryl.

3. A process according to claim 1 in which the compound (2) is prepared by the non-catalytic hydrogenation reduction of the nitroso compound of structure (3) in which $R^1$ and $R^2$ together are an oxygen atom

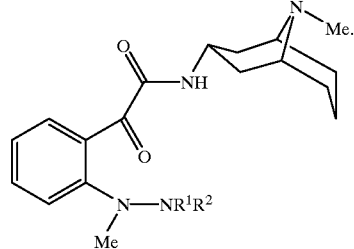
(3)

4. A compound of Structure (2)

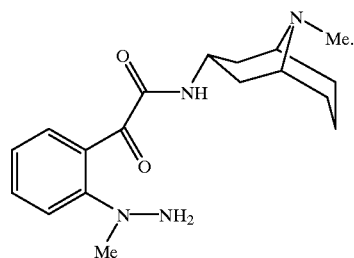
(2)

5. A compound of Structure (3) in which $R^1$ and $R^2$ together form the group =CHR, where R is $C_{1-4}$ alkyl or aryl, or in which $R^1$ and $R^2$ together are an oxygen atom, and salts thereof

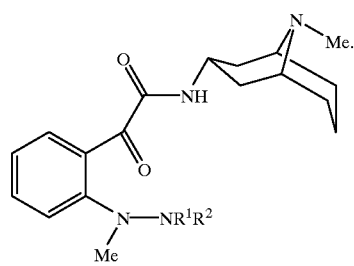
(3)

* * * * *